US 6,533,502 B2

(12) United States Patent
McVay et al.

(10) Patent No.: US 6,533,502 B2
(45) Date of Patent: Mar. 18, 2003

(54) WIRELESS APPARATUS AND METHOD FOR ANALYSIS OF PILES

(75) Inventors: Michael C. McVay, Gainesville, FL (US); Victor H. Alvarez, Gainesville, FL (US); Charles S. Broward, III, Melrose, FL (US); Sidney L. Schofield, Gainesville, FL (US); Sastry Putcha, Tallahassee, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/837,148

(22) Filed: Apr. 17, 2001

(65) Prior Publication Data

US 2002/0148298 A1 Oct. 17, 2002

(51) Int. Cl.⁷ ............................................ E02D 7/00
(52) U.S. Cl. .................. 405/232; 405/229; 73/11.03; 340/853.8
(58) Field of Search ................. 700/108; 73/11.03; 340/853.8; 405/232, 229

(56) References Cited

U.S. PATENT DOCUMENTS

| | | | | |
|---|---|---|---|---|
| 4,365,306 A | * | 12/1982 | House et al. ................. 173/20 |
| 4,586,366 A | * | 5/1986 | Milberger .................. 73/11.03 |
| 5,278,687 A | * | 1/1994 | Jannson et al. .............. 359/124 |
| 5,339,679 A | * | 8/1994 | Ingram et al. ............. 73/152.59 |
| 5,581,013 A | * | 12/1996 | Frederick .................. 73/11.03 |
| 5,589,840 A | | 12/1996 | Fujisawa |
| 5,610,818 A | * | 3/1997 | Ackroyd et al. .......... 356/141.1 |
| 5,825,829 A | * | 10/1998 | Borazjani et al. ........... 332/103 |
| 5,978,749 A | * | 11/1999 | Likins et al. ............... 700/108 |
| 6,160,478 A | | 12/2000 | Jacobsen et al. |
| 6,301,551 B1 | * | 10/2001 | Piscalko et al. ......... 340/853.8 |

FOREIGN PATENT DOCUMENTS

| DE | 29509391 U1 | * | 10/1995 | ............. E02D/7/14 |
|---|---|---|---|---|
| JP | 10102493 A | * | 4/1998 | ............ E02D/13/06 |

OTHER PUBLICATIONS

"Dynamic Testing in Pile Driving Test Program and Production" Stacy et al., and "Sample Specification for Dynamic Testing" by unknown, from www.web.pile.com/Education/694/default.asp?company=; 2000.*

* cited by examiner

Primary Examiner—Heather Shackelford
Assistant Examiner—Katherine Mitchell
(74) Attorney, Agent, or Firm—Akerman Senterfitt (57) ABSTRACT

A system for the determination of pile parameters includes at least one structure for measuring pile data. The structure for measuring pile data is disposed within a measurement range from a pile. A wireless transmitter is communicably connected to the structure for measuring pile data, the wireless transmitter for transmitting the pile data to at least one remotely located receiver. Pile data is preferably encoded in the transmitted data signal. The remotely located receiver is communicably connected to a device for determining at least one pile parameter from the pile measurement data. A method for driving piles includes the steps of wirelessly transmitting pile data to at least one remote receiver, determining at least one pile driving process parameter from the pile data, and driving the pile using the determined pile driving parameter.

48 Claims, 5 Drawing Sheets

WIRELESS APPARATUS AND METHOD FOR ANALYSIS OF PILES

STATEMENT REGARDING FEDERALLY SPONSORED RESEARCH OR DEVELOPMENT

Not applicable.

FIELD OF THE INVENTION

This invention relates to piles generally and, in particular, to a method of and apparatus for the real-time analysis of driven piles.

BACKGROUND

Piles are commonly used to support a wide variety of load bearing structures, such as bridges. Accordingly, piles must be driven to sufficient depths to provide a desired load bearing capacity, without substantially damaging the pile during the driving process. It is customary to characterize pile parameters such as accelerations, strains, pile capacity, stresses within the pile, energy applied to the pile and the average displacement per blow ("blow count") of a driven test pile to determine pile driving process parameters. Pile driving process parameters include the force applied by the driving hammer to the pile and the number of blows required. The force applied by the driving hammer to the pile is referred to as the stroke (or hammer stroke) for a hydraulic hammer and the fuel setting for a diesel hammer. The determined pile driving process parameters are then applied to a plurality of piles during the driving process.

Pile parameters are conventionally measured by mounting sensors on the top of a test pile. The sensors produce raw pile data. Sensor data is supplied to a pile driver analyzer through a hard-wired connection and is used to determine pile parameters which are derived from the supplied raw pile data. Pile driving analyzers can each cost approximately $40,000 to $100,000.

Accelerometers are sensors which are generally used to measure pile acceleration, which can be converted (through integration twice) into the displacement of piles being driven (e.g. into the earth) by a pile driving hammer. An accelerometer is typically mounted near the top of a test pile, the accelerometer wired to an analyzer, such as a pile driver analyzer. From raw pile data, the pile driving analyzer can determine the efficiency of the pile driving hammer, accelerations, driving resistance of the pile (capacity), stresses in the pile as well as other useful pile parameters. In the case of capacity, soil resistance results from both the sides and the tip (bottom) of the pile, the soil resistance being a function of pile depth.

Conventional systems for measuring driving resistance and pile velocity (which can be integrated to produce displacement) utilize self-generating-type accelerometers, which, as the name implies, self-generate direct current electric signals. A quartz or piezoelectric crystal is compressed by the forces generated by the mass of the accelerometer during movements of the pile, producing electrical impulses which are proportional to the acceleration of the pile. The acceleration signals produced by the accelerometer mounted on a test pile are recorded and subsequently electronically integrated through a wired connection to separate equipment (e.g. pile driver analyzer) to produce a velocity measurement. The velocity measurements are in turn, electronically integrated a second time to produce a measurement of pile displacement. The number of recorded blows are determined for each linear unit of displacement to arrive at the blow count.

The force applied to the pile by the pile driving hammer is generally sensed simultaneously by separate apparatus, such as a strain gauge. A strain gauge may be mounted near the top of a test pile disposed orthogonal to the accelerometers. The strain gauge is wired to an analyzer, such as a pile driver analyzer, and used to determine strains, stresses and forces. The force and average displacement can be converted by an analyzer into a driving resistance by known formulas which recognize soil conditions, pile configuration and desired depth of penetration.

As a pile is driven into a material (e.g. earth), the force of the blows applied must also be controlled to avoid exceeding the elastic limit of the pile material. Otherwise, costly damage to the pile can occur, such as to the pile tip or to any portion of the pile length due, for example, to the vibrational energy transmitted by the back reflected wave. To help minimize such damage, drive caps are fitted over the head of the pile to more evenly transmit the hammer blows to the pile and to cushion the blows, while at the same time maintaining the head of the pile in alignment with the hammer by guiding the head parallel to the leads frame and retaining the pile in a substantially straight predetermined path.

Although the use of caps (e.g. steel caps) with cushions and maintaining proper alignment of the hammer and the pile with the aid of leads helps to mitigate pile damage, the burden in most cases falls largely upon the experience of the operator to determine the driving force required. For a given set of conditions, one or more test piles may be used to help guide the operator. Strain gauges mounted on sample piles are commonly used to determine the force of blows and the dynamic forces within piles.

However, strain gauges can fail to register the presence of transmitted waves. For example, two waves can destructively interfere at any point along a pile so that no net stress results when a forward wave is met by a back reflected wave having an equivalent magnitude. Specifically, a compressional wave pointing down the pile can be offset in whole or in part by a tension wave pointing up the pile. In the case of two or more waves which offset, a device capable of measuring pile displacement, such as an accelerometer, can be used to identify the stressless dynamic condition.

Strain gauges must generally be screwed or otherwise attached to the pile and wired to a pile driving analyzer. Thus, the process of properly mounting strain gauges is a relatively time consuming and costly process. The strain gauge is also generally a very fragile device and its reliability under the repetitive dynamic shock loading to which the pile is subjected can be easily compromised.

Even after a pile is driven to a desired depth based on data derived from a test pile, it is generally desirable to measure the actual static bearing load which the driven pile can support mainly because of variability in the ground condition. This is usually done by loading a test pile with increasing weight until it moves. This is called a dead load bearing test, which is a time-consuming and expensive process.

As noted earlier, piles driven subsequent to the test pile are generally driven without measuring pile parameters during the driving process. Due to variation in parameters such as the ground condition between areas within a given construction area, piles tend to be driven less or more than the test pile under the same pile driving process parameters (e.g. number of blows and stroke). This can result in undesired results such as loss in capacity and unnecessary expense or pile damage, respectively. In addition, since sensors are also not generally provided to piles which are placed in field service, pile integrity cannot be measured during the service lifetime of piles. Accordingly, damaged piles, which can potentially lead to the collapse of a structure supported by the damaged pile, are typically not detectable while the pile is in service.

SUMMARY OF INVENTION

A system for the determination of pile parameters includes at least one structure for measuring pile data, the structure for measuring pile data disposed within measurement range from at least one pile. A wireless transmitter is adapted to transmit the pile data, the wireless transmitter communicably connected to the structure for measuring pile data. At least one remotely located wireless receiver is provided for receiving the transmitted pile data.

The system can include a device for determining at least one pile parameter from the pile data, the device being communicably connected to the remotely located wireless receiver. The structure for measuring pile data can include at least one strain gauge. Transmissions from the wireless transmitter can include information which can be identified with the location of specific piles.

The transmitter can be a broadband transmitter, and the system can include a multiplexer for combining pile data from a plurality of structures for measuring pile data into one signal for transmission. Structures for measuring pile data can be positioned substantially within piles.

The system can further include a wireless receiver adapted to receive triggering signals, receipt of the triggering signals directing the structure for measuring pile data to commence measurement of pile data. Structures for measuring pile data can be adjacent to a bottom portion of the pile and/or positioned adjacent to a top portion of the pile. At least one structure for measuring pile data can be disposed between the structure for measuring pile data adjacent to a bottom portion of the pile and the structure for measuring pile data adjacent to a top portion of the pile. When at least one structure for measuring pile data is positioned adjacent to a bottom portion of the pile, the structure for measuring pile data adjacent to a bottom portion of the pile can be positioned below the ground level. In a preferred embodiment of the invention, pile data can be digitally encoded prior to transmission by the wireless transmitter.

An apparatus for supporting load bearing structures includes at least one pile and at least one structure for measuring data from the pile. The structure for measuring pile data as disposed within measurement range from the pile. A wireless transmitter is communicably connected to the structure for measuring pile data. At least one remotely located wireless receiver is provided for receiving the transmitted pile data. The system can further include a device for determining at least one pile parameter from the pile data, the device communicably connected to the remotely located wireless receiver. The structure for measuring pile data can include at least one strain gauge. Transmissions from the wireless transmitter include information which can be identified with the location of specific piles.

The wireless transmitter can be a broadband transmitter and the apparatus can further include a multiplexer for combining pile data from a plurality of the structures for measuring pile data into one signal for transmission. In a preferred embodiment of the invention, pile data is digitally encoded prior to transmission by the wireless transmitter.

At least one of the structures for measuring pile data can be positioned substantially within the pile. The pile can have at least one open volume within the pile, the open volume adapted for receipt of the structure for measuring pile data. The volume with the pile can include at least one longitudinally oriented volume. The apparatus can further include a wireless receiver adapted to receive triggering signals, the receipt of triggering signals directing the structure for measuring pile data to commence measurement of pile data.

At least one structure for measuring pile data can be positioned adjacent to a bottom portion of the pile and/or at least one structure for measuring pile data can be positioned adjacent to a top portion of the pile. When structures for measuring pile data are positioned on both top and bottom positions of a pile, at least one structure for measuring pile data can be disposed between the structures for measuring pile data. At least one structure for measuring pile data can be positioned adjacent to a bottom portion of the pile, the structure for measuring pile data being below the ground level.

An apparatus for supporting load bearing structures includes at least one pile and at least one structure for measuring pile data. At least one of the structures for measuring pile data is mounted to or substantially within the pile. A transmitter is provided which is communicably connected to the structure for measuring pile data. The transmitter can be wireless transmitter, the wireless transmitter for transmitting pile data to at least one remotely located receiver. The transmitter can be a broadband transmitter, and the apparatus can also include a multiplexer for combining pile data from a plurality of structures for measuring pile data into one signal for transmission. In a preferred embodiment of the invention, pile data can be digitally encoded prior to transmission by the transmitter. The receiver can be communicably connected to a device for determining at least one pile parameter from the pile data.

A system for the measurement of pile parameters, includes a pile and at least one structure for measuring pile data. At least one of structure for measuring pile data is mounted substantially to or within the pile. A transmitter is communicably connected to the structure for measuring pile data for transmitting pile data to at least one remotely located receiver. The remotely located receiver is communicably connected to a device for determining at least one pile parameter from the pile data. The transmitter can be a wireless transmitter.

The transmitter can be a broadband transmitter and the apparatus also include a multiplexer for combining pile data from a plurality of structures for measuring pile data into one signal for transmission. In a preferred embodiment of the invention, pile data can be digitally encoded prior to transmission by the transmitter.

At least one structure for measuring pile data can be disposed substantially at the bottom end of the pile. The structure for measuring pile data disposed at the bottom of the pile can be mounted substantially within the pile.

A method of forming piles with sensors mounted substantially within includes the steps of providing at least one sensor for measuring pile data, positioning the sensor in a location which will be substantially surrounded by pile material after application of the pile material, and substantially surrounding the sensor with the pile material. The sensor can be positioned at an interior location in a pile frame in the positioning step.

The surrounding step can include a casting step. The providing step can include providing a transmitter, the transmitter communicably connected to the sensor. The transmitter can be a broadband transmitter, and the providing step can further include a multiplexer for combining pile data from a plurality of the structures for measuring pile data into one signal for transmission.

A method for the wireless determination of pile parameters includes the steps of providing at least one structure for measuring pile data, the structure for measuring pile data within measurement range from a pile, and a wireless transmitter communicably connected to the structure for measuring pile data, and wireless transmitting the pile data to at least one remote receiver by the wireless transmitter. The method can further include the steps of providing the received pile data from the remote receiver to a computing device, and determining at least one pile parameter by the computing device. Preferably, the transmitting, the directing and the determining steps are automatic. The determining step can further include using the pile parameters determined in the determining step to determine at least one pile driving process parameter for use during pile driving. The pile driving process parameter can include a force applied by a driving hammer to a pile.

The pile can support a structure, wherein the transmitting, the directing and the determining steps are performed after installation of a pile. The transmitting, directing and the determining steps can be performed real-time and can be performed responsive to a received excitation signal. The received excitation signal can have a threshold. Above a predetermined threshold excitation to the transmitting, directing and determining steps are initiated. The received excitation can include information which can be identified for selective processing by specific piles. Transmissions during the transmitting step can include information for determining the location of specific piles and the method can further include the step of determining the location of specific piles from received pile data transmissions. The method can further include the step of using at least one of the determined pile parameters to determine at least one pile driving parameter.

A method for driving piles includes the steps of providing at least one structure for measuring pile data, the structure for measuring pile data within measurement range from a pile and a wireless transmitter communicably connected to the structure for measuring pile data. Pile data is wirelessly transmitted to at least one remote receiver by the wireless transmitter and at least one pile driving process parameter is determined from the pile data. The pile is driven using the pile driving process parameters. The wirelessly transmitting and the determining steps can be performed automatically. The driving step can be automatic. The pile driving process parameters can include a force applied by a driving hammer to the pile. The method can include the step of adjusting the force applied between blows of a driving hammer. The step of adjusting the force applied can be based at least in part on determined pile parameters.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION

In conventional pile driving, a test pile is driven, monitored and pile parameters determined for use by trained personnel (e.g. engineer). The trained personnel determine various pile driving process parameters, such as the hammer stroke and number of blows which are to be applied to a plurality of piles from the determined pile parameters. Thus, pile driving process parameters are generally determined on a sample basis by mounting sensors to the top of a test pile and hard-wiring the sensors to a costly pile driver analyzer. The sensors transmit raw stress and acceleration data over a wire lead to the analyzer. Sensors are not conventionally mounted on the tip (bottom) of piles because the required wireline connection to an analyzer device would be almost certainly damaged during the driving of the pile into the surroundings (e.g. earth).

Due to the above method, piles driven subsequent to the test pile are driven without measuring pile parameters during the driving process. Due to variation in some parameters, such as the ground condition between areas within a given construction site, use of a given set of pile driving conditions determined from the test pile will result in some piles being driven less than the test pile, while some piles will be driven more than the test pile. This variability in earth conditions can result in a loss in capacity if underdriving occurs, or unnecessary expense or pile damage if overdriving occurs. Importantly, engineers generally apply a significant factor of safety in the pile driving process parameters selected to avoid pile damage by using a force applied by a driving hammer that is low enough to ensure that substantially all piles are undamaged from the driving process. Unfortunately, a less than optimum hammer stroke results in inefficiency (e.g. more strokes) required in a driving process.

Figure 1:
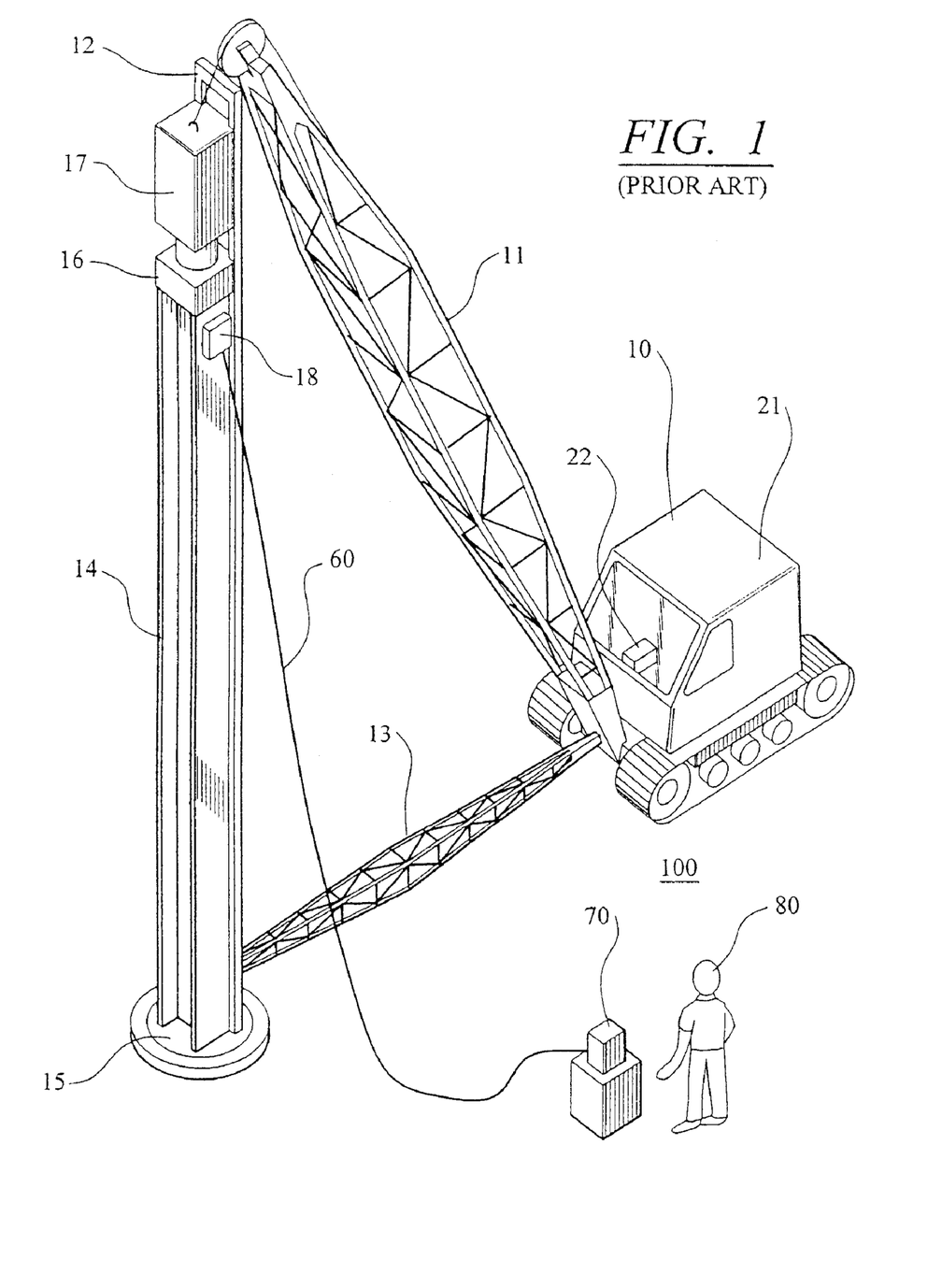
FIG. 1 illustrates a prior art pile driving test system.

Referring to FIG. 1, a view of a conventional pile driving test system 100 includes a crane 10 on which is mounted a boom 11, which is mounted to swivel at its upper end by hammer leads 12, and at its lower end by a bottom brace 13. The test pile 14, which is shown in a position prepared to be driven into the earth, is supported at its lower end by the ground at the point generally denoted as 15, and at its upper end by the drive cap 16 which is slidably associated with the leads 12 so that the cap maintains the pile 14 in alignment with the leads.

The drive cap is arranged to slide down as the pile is driven into the ground. Supported adjacent to the top of the leads and above the drive cap is a pile driving hammer 17, such as a hydraulic hammer, which is slidably associated with the leads and arranged to follow the drive cap 16 and pile 14 as the pile is driven into the ground as indicated. Mounted near the top of the test pile 14 is transducer 18. Electrically connected to transducer 18, is an electrical cable 60 which delivers electrical data signals obtained by transducer 18 (e.g. voltage) to an analyzer device, such as spectrum analyzer 70. An engineer (or technician) 80 interprets data determined by analyzer device 70 to formulate the pile driving process parameters to be used for subsequent piles to be driven by pile driver hammer 17. In conventional pile driving systems, approximately every tenth pile is a test pile.

In one embodiment of the invention, a pile includes at least one sensor for measuring data from the pile and a wireless transmitter communicably connected to the sensor. As used herein, the term "pile" is defined broadly to include all load bearing supporting members such as piers (e.g. to support bridges), columns (to support buildings), shafts and conventional piles, whether pre-cast or cast in-situ. It is noted that columns and shafts are generally not driven, except in the case of load testing a shaft. Accordingly, aspects of the invention related to the driving of a pile to reach a given depth into the surroundings will generally refer to conventional piles and piers. However, it is noted that supporting elements which are cast in-situ such as shafts, may in certain applications be driven into the surroundings after formation.

Piles can be formed from any material capable of supporting a load such as cement, steel, wood or various high strength polymeric materials. Pile materials may include reinforcing materials or structure, such as rebar in the case of concrete.

Sensors are positioned within a "measurement range" from the pile. As used herein, the term "measurement range" is defined to be within a specific distance relative to the pile, the specific distance equal to the furthest distance in which useful pile data can be obtained, depending on the method of pile measurement and the parameter(s) being measured. Thus, the measurement range can include locations within the pile, on the pile, or separated from the pile by a given separation distance. Although mechanical type-sensors will generally require mounting on, or adjacent to the pile, to permit sensing the desired data, methods such as optically based methods (e.g. laser) can permit remote measurement of pile data (e.g. strain and acceleration data). For example, strain and acceleration data can be remotely obtained at or near the pile top using optical methods, since the top of the pile is exposed both during and after driving.

It may also be possible to perform remote data measurement from the pile tip (bottom), even if the tip is disposed below ground level, by using optical techniques combined with a pile having one or more paths for the light. As used herein, "light" means not only signals in the spectrum of visible light, but also signals in the full spectrum of frequencies typically handled by optical transmission systems (e.g. ultraviolet, infrared, etc.). For example, the pile can be formed having coupling light channels and optical mirrors positioned within the pile to permit an externally applied optical beam to reach the pile tip and return to a detector positioned external with reference to the pile.

Sensors used in the wireless embodiment of the invention are communicably connected to at least one wireless transmitter. Sensor data is generally captured as analog data (e.g. a voltage level corresponding to a force). Although pile data can be processed and transmitted as analog signals, analog signals generally produce high levels of noise in the transmissions which can lead to errors in parametric determinations based on received pile data.

Preferably, if analog data is acquired by sensing devices, the analog data is digitized into bit streams using analog to digital (A/D) converters, and digitally filtered and encoded by a suitable device, such as a digital signal processor (DSP). This process is analogous to signal processing applied to voice signal in digital cellular communications. One or more modulated digital signals (e.g. from multiple sensors) each having pile data can be combined into a single digital signal using a multiplexer, converted to an analog signal using a digital to analog (D/A) converter, up-converted in frequency (e.g. a local oscillator), and supplied to a broadband transmitter connected to an antenna for the wireless emission of a single multiplexed signal having the sensor information digitally encoded therein. In the preferred embodiment of the invention, emitted signals are transmitted at a carrier frequency from approximately 900 MHZ to 2.4 GHZ. Emitted signals may also utilize spectral efficiency techniques known in the art such as time multiplexing (TDM), code division multi-access (CDMA), or other known spectral efficiency enhancing methodologies.

Emitted signals can include information to permit pile location to be determined from receipt of the signal. Specific carrier frequencies can be identified with specific piles. Transmitters can also be equipped with GPS. Alternatively, emitted signals from individual piles can include unique tones which can be identified with individual piles by reference to a registration list. Transmitted signals can include unique internet protocol (IP) type addresses permitting identification by reference to a registration list. Time multiplexing can also provide a method for identification of individual piles from the time of receipt of time synchronized signals, where multiple pile transmitters can share a given carrier frequency. Many other methods which permit pile location information to be determined from a received signal will be apparent to ones skilled in the art.

Pile sensors generally include at least one strain gauge and at least one accelerometer. However, as noted earlier, information provided by strain gauges and accelerometers may be generated using optical methods. Assuming a strain gauge is used, strain gauge data can be used to determine strains, stresses and forces induced in the vertical (height) axis of the pile. The vertical pile strains, stresses and forces can be oriented downward or upward along the height axis of the pile. Although not generally required, it may be helpful to include strain gauges to permit the determination of strain, stress and forces along one or both axes transverse to the height axis of the pile.

If the strain gauge is placed near the center of the cross sectional area of a pile, one strain gauge is generally sufficient for most applications. However, two (or more) strain gauges sensitive along the same axis (e.g. vertical axis) can be used to improve the repeatability of measurements by permitting statistical techniques, such as averaging of measured pile data. An accelerometer is generally required to provide acceleration data, from which acceleration, velocity and displacement data can be determined. However, an accelerometer may not be necessary to measure acceleration data if two or more strain gauges are provided. For example, two strain gauges located a fixed distance apart will generally receive a given signal at different times. From knowledge of the separation distance between the gauges, the velocity can be calculated from the known distance divided by the measured arrival time of the waves at the respective strain gauges.

Many types of strain gauges and devices for measuring displacement, velocity and accelerations of piles can be used with the invention. For example, foils, vibrating wires, fiber optics, pressure transducers (piezo-electric, piezo-resistive, or piezo-capacitance), potentiometers and variable reluctance strain gauges, or other strain gauges known in the art, may be used with the invention.

A variety of types of available instrumentation can be used to measure acceleration data within the pile. Accelerometers are commonly used for this purposes. Accelerometers include piezo-electric, piezo-resistance, piezo-capacitance types. Alternatively, LVDTs (linear variable differential transformer) can be used. In the preferred embodiment of the invention, piezoelectric accelerometers are used because of their "G level" sensitivity is in the desired range of 200 to 1,000 Gs.

Sensors are communicably connected to the transmitter provided. Communicably connected can include various forms of data communication, such as optical (e.g. laser), wired electronic, wireless electronic, vibrational. In the case of a concrete pile having sensors embedded within, rebar can be added to the pile to facilitate wireless electronic transmissions.

In conventional systems, sensors are fastened (e.g. screwed) to the top of test piles. Because of wireline connections between sensors and the analyzing device, conventional sensors cannot be placed on the bottom of the pile. Using the invention, sensors can be placed anywhere along the length of the pile, including within the pile at the bottom of the pile, the bottom being subject to being disposed under the ground level in field applications. Providing sensors positioned at or near the bottom of piles (hereafter "bottom sensors") can produce valuable data that cannot be obtained from sensors mounted on the top of the pile.

Figure 2:
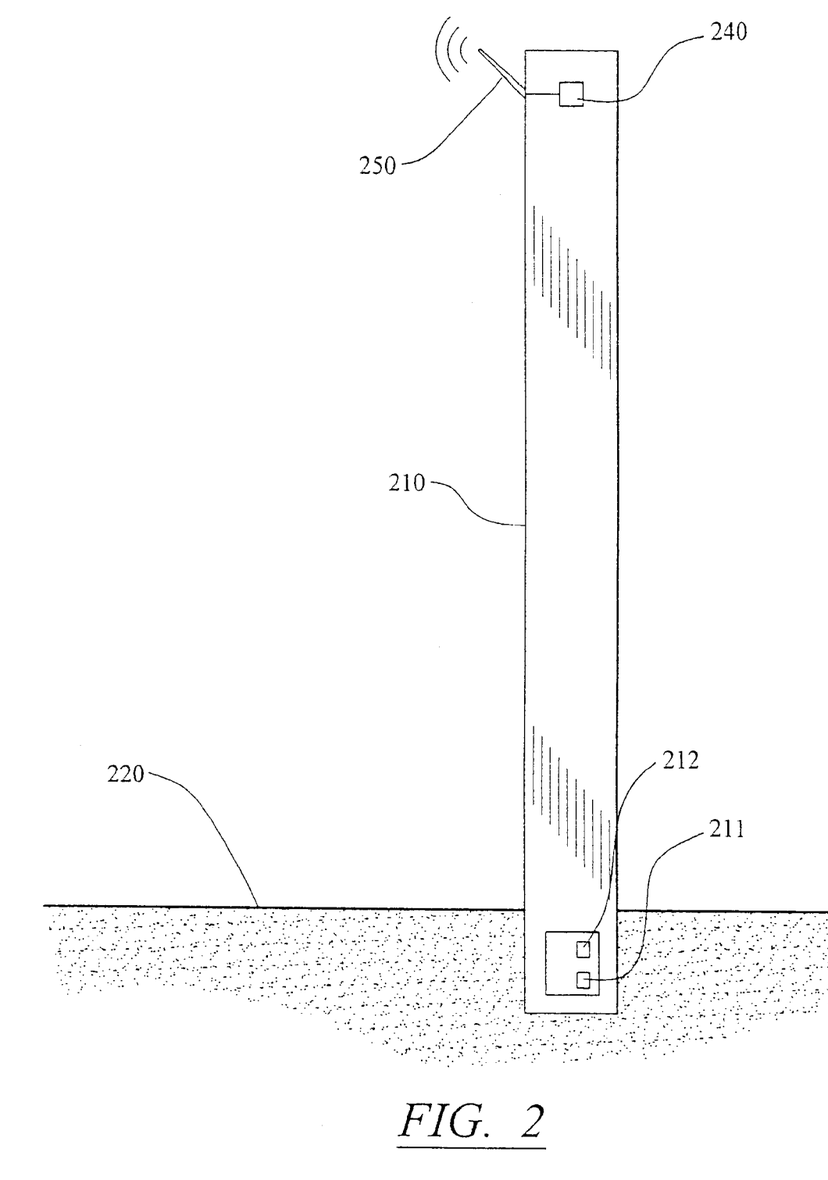
FIG. 2 illustrates a pile after driving having sensors below the ground level, according to an embodiment of the invention.

Referring to FIG. 2, a pile having bottom sensors including strain gauge 211 and accelerometer 212 are disposed substantially within pile 210, such as concrete pile. Strain gauge 211 and accelerometer 212 are located below the level of the ground 220, such as the resulting position following driving or pushing. Sensor data from strain gauge 211 and accelerometer 212 are supplied to transmitter/amplifier 240 for emission by a suitable structure for emission, such as antenna 250. Preferably, signal processing elements (not shown) digitize, encode and combine sensor data, so that a single RF emitted signal can carry data derived from two or more sensors, such as strain gauge 211 and accelerometer 212.

Specifically, using pile data derived from bottom sensors that are disposed within the ground or other host material, it is possible to separate the skin friction and tip resistance components of pile capacity. Residual stresses in piles can also be measured in the pile following the driving process by having a strain gauge positioned near the bottom of the pile. Knowledge of the residual stress prior to loading piles permits a more accurate determination of the change in skin friction and tip resistance resulting from an applied load.

In the preferred embodiment of the invention, piles are each provided with affixed or otherwise permanent sensing devices, so that field pile data can be taken while the piles are being driven as well as when piles are in field use. The ability to separately monitor skin friction permits the effects of external influences such as water (scour) and earthquakes to be quantified for each pile, while the pile is in service in the field. As a result, using permanently positioned bottom sensors, dynamic weakening effects such as the scour of piles supporting bridges can be monitored. If weakening is detected, affected piles can be replaced prior to the occurrence of a potentially catastrophic collapse.

Figure 3:
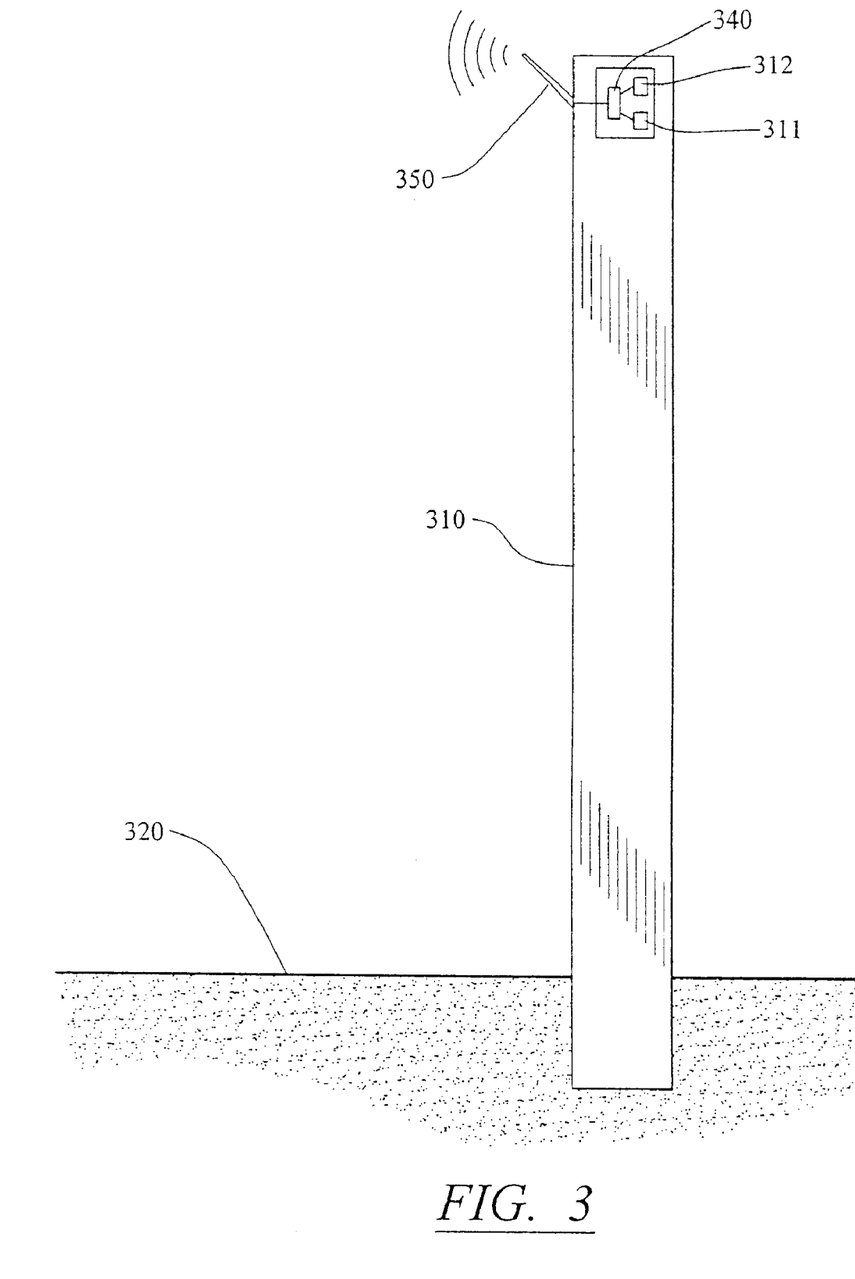
FIG. 3 illustrates a pile having sensors embedded substantially within the pile and a wireless transmitter, according to an embodiment of the invention.

Referring to FIG. 3, a preferred embodiment of one aspect of the invention having a pile with embedded sensors and a wireless transmitter is shown. Strain gauge 311 and accelerometer 312 are embedded in a casted pile 310, such as a concrete pile. Sensor data from strain gauge 311 and accelerometer 312 are output by transmitter/amplifier 340 preferably as a single RF signal having encoded digital measurement data from both strain gauge 311 and accelerometer 312. Antenna 250 emits sensor signals which permits reception by one or more remote receiving stations (not shown) for parametric determinations from the received sensor data.

Figure 4:
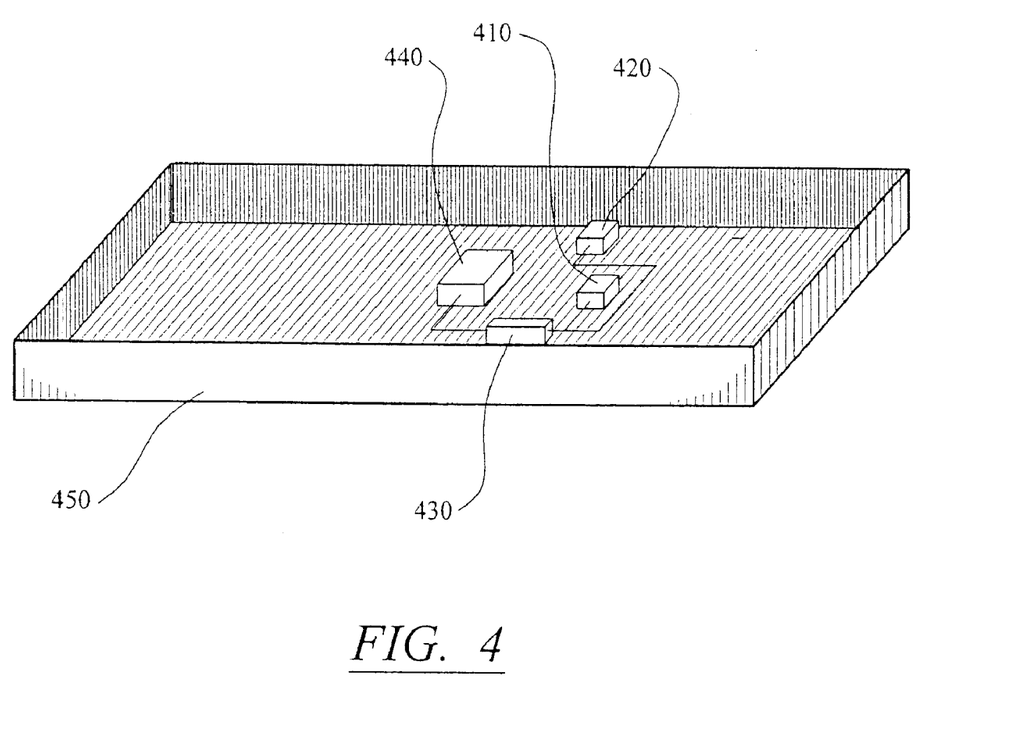
FIG. 4 illustrates pile measurement instrumentation including a strain gauge, accelerometer, power supply and a transmitter positioned within a pile shell prior to being cast substantially within a concrete pile, according to an embodiment of the invention.

FIG. 4 shows a strain gauge 410, accelerometer 420, power supply 430 and transmitter 440 positioned in frame 450 prior to being cast substantially within a pile, such as a concrete pile. Although wireline connections are shown between the sensors 410 and 420 and transmitter 440, the invention is in no way limited to wireline connection between sensors 410 and 420 and transmitter 440. For example, communication by sensors 410 and 420 to transmitter 440 can be through the pile material (e.g. concrete with metal rebar), rather than through an electrically conductive wire. Alternatively, the connection between sensors 410 and 420 and transmitter 440 can be optical (e.g. fiber optic).

Alternatively, piles can be formed which provide access to one or more volumes void of pile material to permit sensor placement (and sensor replacement) after pile formation. For example, a cylindrical pile can be formed with one or more longitudinal openings, such as a hollow pile center region to permit sensor placement, and if required, sensor replacement.

Batteries can be supplied to power the pile measurement apparatus. To conserve power, the measurement apparatus can be placed in a low power, idle mode, while awaiting a wake up signal. Upon receipt of an appropriate triggering wakeup signal, updated pile data can be taken and transmitted to one or more receiver sites. Alternatively, the apparatus can include a timer. Upon expiration of the timer, updated pile data can be taken and transmitted to the receiver sites.

Power can be supplied externally to the apparatus. For example, piles can be equipped with solar panels to produce electricity. Energy can also be supplied to the measurement system over the air and received by an antenna device. A suitable storage device (e.g. battery) can preferably be used to store externally supplied power.

The measurement system can also be enclosed (not shown) with a suitable water resistant (e.g. polymeric) or preferably waterproof covering to create a "potted" pile measurement apparatus. In applications subject to corrosive environments, such as around water, a potted apparatus is preferred.

Potted apparatus may preferably be combined with positioning the potted apparatus substantially within piles. For example, potted sensors may be positioned on prestressing strands within a pile frame prior to a casting step. In this embodiment, following the casting step, the potted measurement apparatus can be substantially surrounded by pile material (e.g. concrete).

Figure 5:
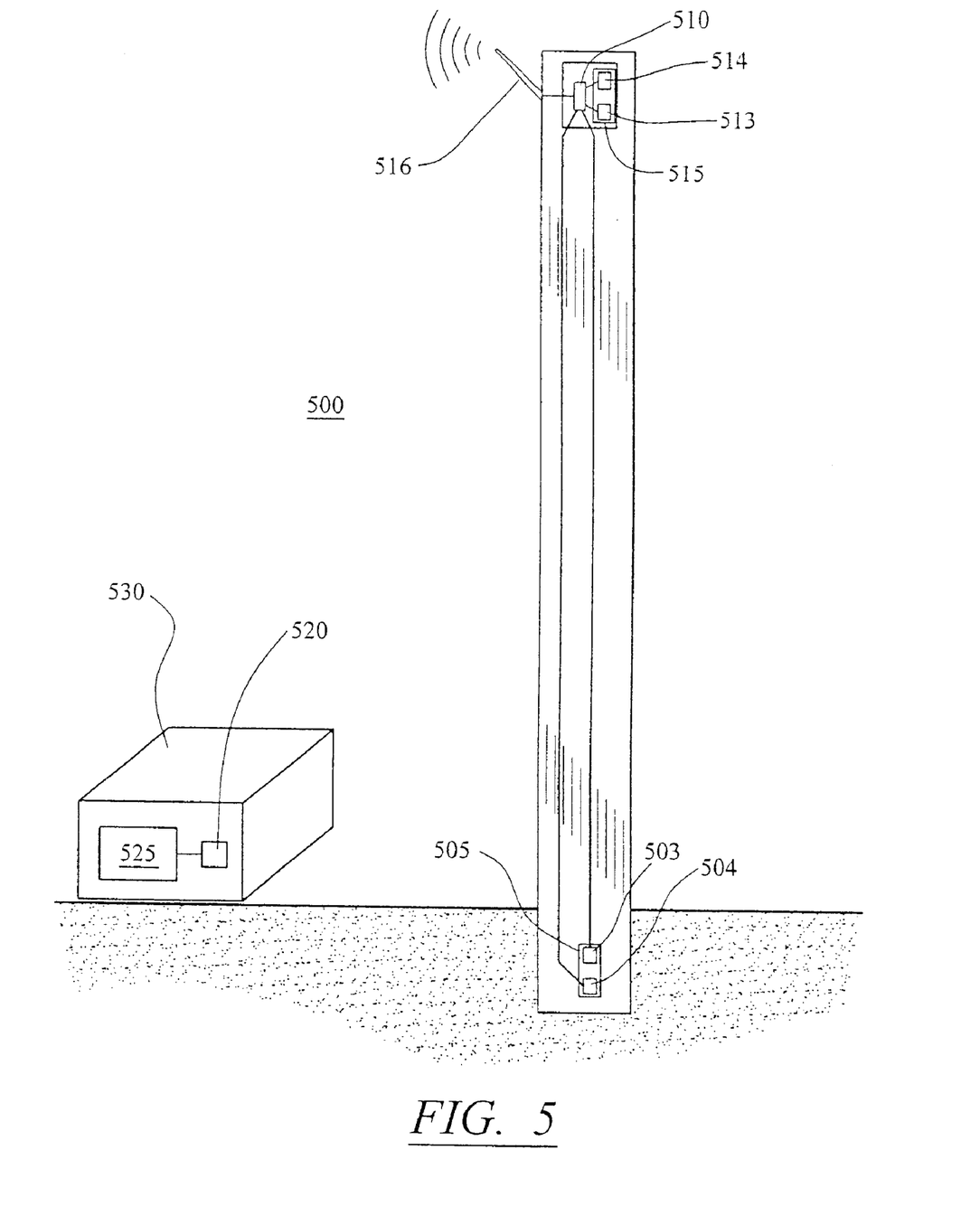
FIG. 5 illustrates a pile measurement system for the determination of pile parameters and pile driving process parameters, including a wireless transmitter, according to yet another embodiment of the invention.

FIG. 5 shows a system 500 for the determination of pile parameters, which includes at least one structure 505 for measuring pile data adapted for subsurface measurements, the subsurface structure for measuring pile data including strain gauge 503 and accelerometer 504. Pile data measurement structure 505 is preferably a potted apparatus having a suitable covering material (not shown). Near the pile top a second pile measurement structure 515 can include strain gauge 513 and accelerometer 514. A wireless transmitter 510 is communicably connected to the sensors comprising structures for measuring pile data 505 and 515, the wireless transmitter 510 for transmitting pile data via antenna 516 to at least one remotely located receiver 520. The receiver is communicably connected to a computing device 525 for determining at least one pile parameter from the received pile data. Computing device 525 can be a lap-top computer, or any other appropriate computing device. Remote receiver 520 and computing device 525 are disposed within remote facility 530.

Using appropriate software, computing device 525 can determine pile parameters such as the total capacity, deformations, stresses, strains, forces, accelerations, energy transmitted in the pile, vibration magnitudes and vibration frequencies as well as pile driving process parameters, such as the force applied by the driving hammer to the pile. Pile parameters and pile driving process parameters can be computed by computing device 525, and pile driving process parameters can be transmitted from computing device 525 by a suitable transmitter (not shown) for use by a site engineer, a hammer operator, or preferably by an automated apparatus for use during pile driving operations. Pile parameters and pile driving process parameters are most preferably determined by obtaining updated acceleration and strain data each time the hammer strikes the pile head, the updated pile driving process parameters supplied to a control device (not shown) which controls the pile driving hammer (not shown). For example, if stresses within the pile are below some predetermined threshold during a given blow, the energy applied to the pile by the pile driving hammer can be increased on the subsequent blow by increasing the force applied by the driving hammer. In addition, the ability to measure pile capacity on a blow by blow basis permits driving until a desired pile capacity results. However, piles may continue to be driven, even after reaching a desired capacity if the pile has not yet reached a depth at or beyond a cutoff depth. An accelerometer typically is used to measure the depth reached by piles. Minimum cutoff depths are used to impact a safety factors for piles against pile capacity reducing effects such as scour and liquidification.

Using the same apparatus described above, pile parameters can be determined by computing device 525 from pile data transmitted by transmitter 510 during field use piles. Thus, pile integrity may be monitored during field service while piles are supporting loads.

The ability to obtain and process post-installation pile data can be used to monitor pile integrity over the service lifetime of piles. For example, pile damage can be detected through the measurement of pile parameters (e.g. stresses and strains), which can result from catastrophic events. For example, piles can be damaged by events such as hurricanes, earthquakes, or impacts (e.g. boats). In addition, the invention can be used to monitor damage to existing structures due to nearby construction activity.

Moreover, the ability to determine post-installation pile parameters permits accurate measurement of pile capacity which can increase during the days following installation due to the "freeze" effect. The freeze effect results principally from the decrease in pore pressure when excess water substantially leaves the soil surrounding piles in the days after driving. Granular soils typically freeze after one or two days, while clay soils generally requiring a longer period of time to freeze.

The invention can be particularly useful when applied to foundation elements, particularly deep foundation elements. If a measurement apparatus according to the invention is installed in deep foundation elements, the applied factor of safety used during driving can be significantly reduced by measurement of actual foundation element parameters for each element during driving, preferably on a blow by blow basis. This can lead to optimized use of the hammer (higher stroke) which is made possible by increasing the stroke on a blow by blow basis while monitoring damage to the foundation element. Thus, the invention can provide a significant reduction in foundation costs.

The invention can be applied to numerous segments of the transportation infrastructure. For example, driving parameters for supporting elements for highways, ports, railroads, airports can be determined and utilized during driving. In addition, driven supporting elements can be monitored for structural integrity throughout their lifetimes. The monitoring can be continuous monitoring, or updated on a periodic basis.

The remote facility 530 for receiving and processing pile measurement data can be located anywhere in the world without the need for a data collector to visit the job site. Data can also be transmitted to multiple locations simultaneously. Using currently available technology, data can be transported over data pathways such as the Internet, permitting data to reach distant locations in a fraction of a second.

The remote facility 530 can also transmit information to the construction site, such as pile driving process parameters, based on receipt of pile measurement data and determination of pile parameters by computing device 525. Received pile driving process parameters can be used to direct driving operations. Thus, a feedback and control network can be created.

To accommodate this embodiment of the invention, the system further preferably includes a receiver, signal processors and filters (not shown) to receive at least one pile driving process parameter transmitted by remote facility 530. The receiver, signal processors and filters are preferably communicably connected to a Controller which is communicably adapted to operate a driving apparatus, such as a crane equipped with a hammer. The pile driving information can be supplied by remote facility 530 to provide pile driving process information, such as the hammer stroke, which is adjustable on blow by blow basis in response to determined pile parameters computed by remote computer 525. In the case of a diesel hammer, the hammer stroke will correspond to a fuel setting.

Remote facility 530 can monitor and control driving operations for a plurality of piles simultaneously. It is also possible for remote facility 530 to control other on site activities, such as the location of the crane, etc. Thus, the invention can be used to create a fully automated pile driving system.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A system for the determination of pile parameters, comprising:
   a plurality of sensors including at least one strain gauge for measuring pile data including strain in a pile, said plurality of sensors disposed within said pile;
   a wireless transmitter adapted to transmit said pile data, said wireless transmitter disposed within said pile and communicably connected to said plurality of sensors, and
   at least one remotely located wireless receiver for receiving said transmitted pile data.

2. The system of claim 1, wherein said strain gauge comprises an electrical resistance-type strain gauge.

3. The system of claim 1, wherein said strain gauge is positioned in said pile so as to be disposed below a ground level after said pile is driven or pushed into said ground.

4. The system of claim 1, wherein transmissions from said wireless transmitter include information which can be used to identify a location of said pile.

5. The system of claim 1, wherein said transmitter is a broadband transmitter, further comprising a multiplexer for combining pile data from said plurality of sensors into one signal for said transmission.

6. The system of claim 1, further comprising a water resistant covering, said water resistant for protecting said plurality of sensors and said wireless transmitter.

7. The system of claim 1, further comprising a wireless receiver disposed in said pile for receiving remotely transmitted wireless triggering signals, wherein receipt of said triggering signals prompts said plurality of sensors to commence measurement of said pile data.

8. The system of claim 1, wherein said at least one strain gauge comprises at least a first and a second strain gauge, wherein said first and second strain gauges are disposed in spaced apart relation.

9. The system of claim 8, wherein said first strain gauge is positioned in said pile so as to be disposed below a ground level after said pile is driven or pushed into said ground.

10. The system of claim 9, wherein said first and second strain gauge comprises electrical resistance-type strain gauges.

11. The system of claim 1, wherein said pile data is digitally encoded prior to transmission of said pile data by said wireless transmission.

12. An apparatus for supporting load bearing structures, comprising:
at least one pile;
a plurality of sensors including at least one strain gauge for measuring pile data including strain in said pile, said plurality of sensors disposed within said pile;
a wireless transmitter adapted to transmit said pile data, said wireless transmitter disposed within said pile and communicably connected to said plurality of sensors; and
at least one remotely located wireless receiver for receiving said transmitted pile data.

13. The system of claim 12, wherein said strain gauge comprises an electrical resistance-type strain gauge.

14. The apparatus of claim 12, wherein said strain gauge is positioned in said pile so as to be disposed below a ground level after said pile is driven or pushed into said ground.

15. The apparatus of claim 12, wherein transmissions from said wireless transmitter include information which can be used to identify a location of said pile.

16. The apparatus of claim 12, wherein said wireless transmitter is a broadband transmitter, further comprising a multiplexer for combining pile data from said plurality of sensors into one signal for said transmission.

17. The apparatus of claim 12, wherein said pile data is digitally encoded prior to transmission of said pile data by said wireless transmitter.

18. The apparatus of claim 12, further comprising a water resistant covering for protecting said plurality of sensors and said wireless transmitter.

19. The apparatus of claim 12, wherein said pile has at least one open volume within said pile, said open volume adapted for receipt of said plurality of sensors and said wireless transmitter.

20. The apparatus of claim 19, wherein said open volume includes at least one longitudinally oriented volume.

21. The apparatus of claim 12, further comprising a wireless receiver disposed in said pile for receiving remotely transmitted wireless triggering signals, wherein receipt of said triggering signals prompts said plurality of sensors to commence measurement of said pile data.

22. The apparatus of claim 12, wherein said at least one strain gauge comprises at least a first and a second strain gauge, wherein said first and second strain gauges are disposed in spaced apart relation.

23. The apparatus of claim 22, wherein said first strain gauge is positioned in said pile so as to be disposed below a ground level after said pile is driven or pushed into said ground.

24. The apparatus of claim 23, wherein said first and second strain gauge comprises electrical resistance-type strain gauges.

25. A method of forming piles with sensors mounted substantially within piles, comprising the steps of:
providing a plurality of sensors including at least one strain gauge for measuring pile data including strain in a pile;
positioning said plurality of sensors in at least one location which will be substantially surrounded by pile material after substantially surrounding said plurality of sensors with said pile material, and substantially surrounding said plurality of sensors with said pile material.

26. The method of claim 25, wherein said strain gauge is disposed in a location in said pile which will be disposed below a ground level after said pile is driven or pushed into said ground.

27. The method of claim 26, wherein said positioning step further comprises positioning a wireless receiver in said least one location, said wireless receiver for receiving remotely transmitted wireless triggering signals, wherein receipt of said triggering signals prompts said plurality of sensors to commence measurement of said pile data.

28. The method of claim 25, wherein said positioning step further comprises positioning a wireless transmitter in said least one location, said wireless transmitter communicably connected to said plurality of sensors.

29. The method of claim 28, wherein said wireless transmitter is a broadband transmitter, wherein said providing step further comprises providing a multiplexer for combining pile data from said plurality of sensors into one signal for transmission.

30. A method for the wireless determination of pile parameters, comprising the steps of:
providing a plurality of sensors including at least one strain gauge for measuring pile data including strain in a pile, said plurality of sensors disposed within said pile,
and a wireless transmitter adapted to transmit said pile data, said wireless transmitter disposed within said pile and communicably connected to said plurality of sensors, and
wireless transmitting said pile data to at least one remote receiver by said wireless transmitter.

31. The method of claim 30, further comprising the steps of:
supplying said received pile data from said remote receiver to a computing device, and
determining said at least one pile parameter by said computing device.

32. The method of claim 31, wherein said transmitting, said supplying and said determining steps are automatic.

33. The method of claim 32, wherein said determining step further comprises using said pile parameters determined in said determining step to compute at least one pile driving or pushing process parameter for use during driving or pushing piles.

34. The method of claim 33, wherein said pile driving or pushing process parameter includes a force applied by a driving or pushing hammer to said pile.

35. The method of claim 31, wherein said pile supports a structure, wherein said transmitting, said supplying and said determining steps are performed after installation of said pile.

36. The method of claim 35, wherein said transmitting, said supplying and said determining steps are responsive to a received wireless excitation signal.

37. The method of claim 36, wherein said received excitation signal exceeds a predetermined threshold excitation level and is sufficient to initiate said transmitting, supplying and determining steps.

38. The method of claim 36, wherein said received excitation signal includes information which can be identified for selective processing by said pile.

39. The method of claim 31, wherein said transmitting, said supplying and said determining steps are performed automatically.

40. The method of claim 31, further comprising the step of using at least one of said determined pile parameters to determine at least one pile driving or pushing process parameter.

41. The method of claim 30, wherein said transmitting is automatic.

42. The method of claim 30, wherein said transmissions during said transmitting step include information for determining a location of said pile, said method further comprising the step of determining said location of said pile from said transmissions.

43. A method for driving or pushing piles, comprising the steps of:

provinding a plurality of sensors including at least one strain gauge for measuring pile data including strain in a pile, said plurality of sensors disposed within said pile, and a wireless transmitter disposed within said pile, said wireless transmitter communicably connected to said plurality of sensors;

wirelessly transmitting said pile data from within said pile to at least one remote receiver by said wireless transmitter;

determining at least one pile driving or pushing parameter from said pile data, and driving or pushing said pile using said pile driving or pushing parameter.

44. The method of claim 43, wherein said wirelessly transmitting and said determining steps are performed automatically.

45. The method of claim 43, wherein said driving or pushing step is automatic.

46. The method of claim 45, wherein said pile driving or pushing parameter includes a force applied by a driving or pushing hammer to said pile.

47. The method of claim 46, further comprising the step of adjusting said force applied between blows of a driving or pushing hammer.

48. The method of claim 47, wherein said step of adjusting force is related to at least one of said determined pile parameters.

* * * * *